(12) United States Patent
Oh et al.

(10) Patent No.: US 9,631,971 B2
(45) Date of Patent: Apr. 25, 2017

(54) PHOTOACOUSTIC PROBE AND PHOTOACOUSTIC DEVICE HAVING THE SAME

(71) Applicants: SAMSUNG ELECTRONICS CO., LTD., Suwon-si, Gyeonggi-do (KR); SAMSUNG MEDISON CO., LTD., Nam-myeon (KR)

(72) Inventors: Jung Taek Oh, Seoul (KR); Jung Ho Kim, Seoul (KR); Jong Kyu Jung, Seoul (KR)

(73) Assignees: SAMSUNG MEDISON CO., LTD., Nam-Myeon; SAMSUNG ELECTRONICS CO., LTD., Suwon-si (KR)

( * ) Notice: Subject to any disclaimer, the term of this patent is extended or adjusted under 35 U.S.C. 154(b) by 288 days.

(21) Appl. No.: 14/142,001

(22) Filed: Dec. 27, 2013

(65) Prior Publication Data
US 2014/0182385 A1     Jul. 3, 2014

(30) Foreign Application Priority Data
Dec. 27, 2012    (KR) ........................ 10-2012-0154756

(51) Int. Cl.
| G01H 9/00 | (2006.01) |
| A61B 5/00 | (2006.01) |
| G01N 21/17 | (2006.01) |

(52) U.S. Cl.
CPC ............. *G01H 9/00* (2013.01); *A61B 5/0095* (2013.01); *G01N 21/1702* (2013.01)

(58) Field of Classification Search
CPC ..... G01N 29/2418; G01H 9/00; A61B 5/0095
(Continued)

(56) References Cited

U.S. PATENT DOCUMENTS

| 2006/0210440 A1* | 9/2006 | Potyrailo ........... G01N 21/1702 |
| | | 422/82.01 |
| 2007/0015978 A1 | 1/2007 | Kanayama et al. |

(Continued)

FOREIGN PATENT DOCUMENTS

| JP | 2012-086037 | 5/2012 |
| WO | 2011/111572 | 9/2011 |

OTHER PUBLICATIONS

Extended European Search Report dated Apr. 8, 2014, from European Patent Application No. 13199561.5.

*Primary Examiner* — Michael A Lyons
*Assistant Examiner* — Jean Morello
(74) *Attorney, Agent, or Firm* — Staas & Halsey LLP

(57) ABSTRACT

A photoacoustic probe and photoacoustic device implementing the photoacoustic probe may reduce an artifact caused by an ultrasonic wave generated in the photoacoustic probe without mounting a separate device. The photoacoustic probe and photoacoustic device implementing the photoacoustic probe may reduce an artifact by changing a configuration or a structure provided in the photoacoustic probe. The photoacoustic probe may receive a photoacoustic signal generated from an inner material of an object absorbing light of a predetermined wavelength and may include a piezoelectric module to convert the photoacoustic signal into an electric signal, and an object contact unit disposed on the front surface of the piezoelectric module, the object contact unit contacting the object and not absorbing the light of a predetermined wavelength.

24 Claims, 17 Drawing Sheets

(58) Field of Classification Search
USPC .......................................................... 73/655
See application file for complete search history.

(56) References Cited

U.S. PATENT DOCUMENTS

| | | |
|---|---|---|
| 2010/0094134 A1 | 4/2010 | Zhu et al. |
| 2012/0157837 A1 | 6/2012 | Nagata et al. |
| 2013/0064771 A1* | 3/2013 | Wada ................. G01N 21/1702 424/9.1 |

* cited by examiner

PHOTOACOUSTIC PROBE AND PHOTOACOUSTIC DEVICE HAVING THE SAME

CROSS-REFERENCE TO RELATED APPLICATIONS

This application claims the priority benefit of Korean Patent Application No. 10-2012-0154756, filed on Dec. 27, 2012 in the Korean Intellectual Property Office, the disclosure of which is incorporated herein by reference for all purposes.

BACKGROUND

1. Field

Embodiments disclosed herein relate to a structure of a photoacoustic probe to receive a photoacoustic wave generated from a material absorbing light and a photoacoustic device comprising the photoacoustic probe.

2. Description of the Related Art

A medical imaging device, which includes for example, an ultrasonic imaging device, a photoacoustic imaging device, an X-ray imaging device and the like, acquires an image of an object using transmission, absorption or reflection properties of ultrasonic waves, lasers, X-rays or the like with respect to the object and uses the image for diagnosis of a condition of an object or subject.

Photoacoustic imaging may refer to a method for noninvasively obtaining an image of an object using a photoacoustic effect. A photoacoustic effect may refer to a phenomenon in which a material absorbs light or electromagnetic waves to generate an acoustic wave.

In order to obtain a photoacoustic image, a light source to radiate light to an object and a probe to receive a photoacoustic wave generated from an inner material of the object are used. When the radiated light is incident upon the probe, artifacts are disadvantageously created in the photoacoustic image due to scatter materials present in the object.

SUMMARY

Therefore, it is an aspect of the present invention to provide a photoacoustic probe to reduce an artifact caused by an ultrasonic wave generated in the photoacoustic probe without mounting a separate device. The reduction of artifacts may be obtained by changing a configuration or a structure provided in the photoacoustic probe, and a photoacoustic device including the same.

Additional aspects of the invention will be set forth in part in the description which follows and, in part, will be apparent from the description, or may be learned by practice of the invention.

In accordance with an aspect of the present invention, a photoacoustic probe to receive a photoacoustic signal generated from an inner material of an object absorbing light of a predetermined wavelength, includes: a piezoelectric module to convert the photoacoustic signal into an electric signal; and an object contact unit disposed on the front surface of the piezoelectric module, the object contact unit contacting the object and not absorbing the light of a predetermined wavelength.

The photoacoustic signal may be input through the object contact unit into the piezoelectric module.

The object contact unit may include a pigment not absorbing the light of a predetermined wavelength.

The pigment may have a color having a wavelength different from the specific (predetermined) wavelength.

The object contact unit may not include a pigment.

The object contact unit may include a light scattering particle.

The light scattering particle may include titanium dioxide (TiO2), aluminum dioxide (AlO2) and/or silicon dioxide (SiO2).

The light scattering particle may have a submicron size.

The light scattering particle may have a volume ratio of about 6% or less with respect to the object contact unit in order to maintain properties of the photoacoustic signal passing through the object contact unit.

The object contact unit may have a flat shape.

The object contact unit may be an acoustic lens to focus the photoacoustic signal.

In accordance with another aspect of the present invention, a photoacoustic device may include the photoacoustic probe and a light source to irradiate light of a predetermined wavelength to an object.

In accordance with a further aspect of the present invention, a photoacoustic probe to receive a photoacoustic signal generated from an inner material of an object absorbing light of a predetermined wavelength, includes: a piezoelectric module to convert the photoacoustic signal into an electric signal; and an object contact unit disposed on the front surface of the piezoelectric module, the object contact unit contacting the object and not absorbing light of a predetermined wavelength. The object contact unit may include an absorption portion having a higher absorbance to light of a predetermined wavelength and a non-absorption portion having a lower absorbance to the light of a predetermined wavelength, and a contact surface of the absorption portion and the non-absorption portion may have a step structure and the non-absorption portion contacts the object.

The absorption portion may include a pigment absorbing the light of a predetermined wavelength, and the non-absorption portion may include a pigment not absorbing the light of a predetermined wavelength.

The non-absorption portion may have a color having a wavelength different from the specific (predetermined) wavelength.

The non-absorption portion may not include a pigment.

A height of the step may be an odd fold of half of a wavelength of a photoacoustic wave generated by the absorption portion.

The step formed on the contact surface between the absorption portion and the non-absorption portion may be repeated in an irregular period.

The period of the step may be a multiple of the wavelength of the photoacoustic wave generated by the absorption portion.

In accordance with a further aspect of the present invention, a photoacoustic device includes: the above-mentioned photoacoustic probe and a light source to irradiate light of a predetermined wavelength to an object.

In accordance with a further aspect of the present invention, a photoacoustic device includes a probe to receive a photoacoustic signal from an object which absorbs light of a first wavelength, the probe including: a piezoelectric module to convert the photoacoustic signal into an electric signal; and an object contact unit disposed between the piezoelectric module and the object, wherein the object contact unit absorbs light of a second wavelength.

The photoacoustic device may further include a light source to emit light of the first wavelength toward the object.

The object contact unit may include a first color to absorb light of the second wavelength. The object contact unit may include a light scattering particle having a volume ratio of about 6% or less with respect to the object contact unit.

The object contact unit may include an absorption portion and a non-absorption portion, the absorption portion having a higher absorbance to light of the first wavelength than the non-absorption portion. The non-absorption portion may be disposed between the object and the absorption portion, and the non-absorption portion may include a different color than the absorption portion. The absorption portion may be formed with at least one protrusion shaped to fit into at least one groove of the non-absorption portion. The absorption portion may include a second color to absorb light of the first wavelength, and the non-absorption portion may include the first color.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
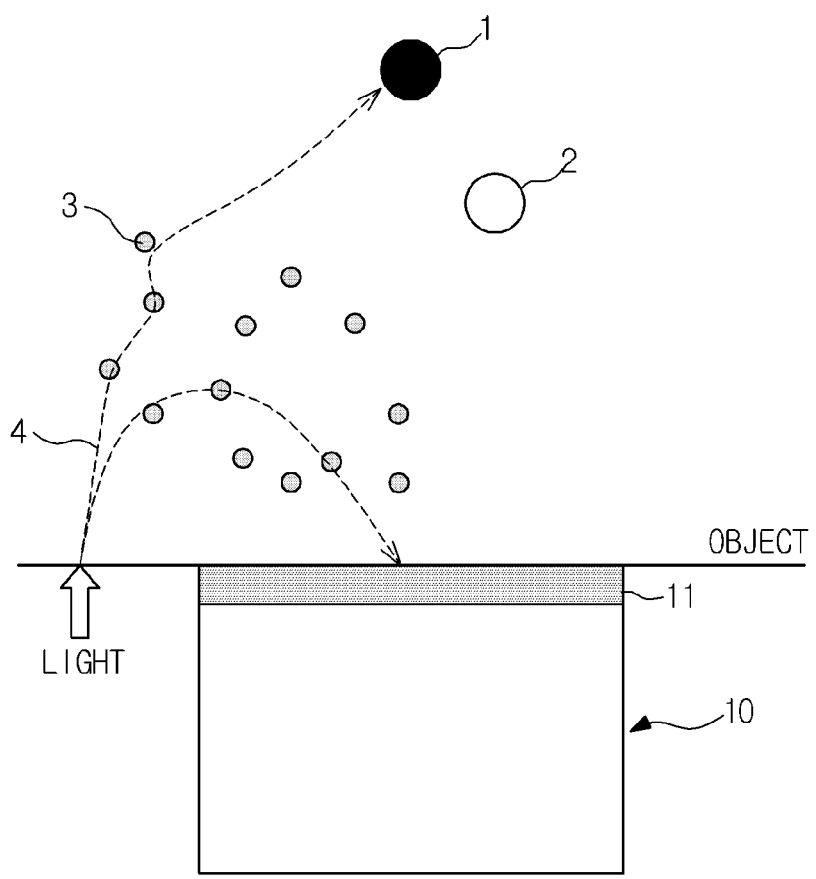
FIG. 1 is a schematic view illustrating a problem occurring when a conventional photoacoustic probe irradiates light to an object.

Reference will now be made in detail to the embodiments of the present invention, examples of which are illustrated in the accompanying drawings, wherein like reference numerals refer to like elements throughout.

Ultrasonic imaging is widely used as a medical imaging method for diagnosing an object. In recent years, photoacoustic imaging in which ultrasonic properties of an object are combined with photoacoustic properties thereof has been developed and utilized in a variety of diagnosis fields.

Photoacoustic imaging (PAI) generally refers to a method in which an ultrasonic image having a high spatial resolution is combined with an optical image having a high contrast ratio, which is suitable for imaging biological tissues. When a laser is irradiated to biological tissues, a short electromagnetic pulse of the laser is absorbed in the biological tissues and a momentary acoustic pressure is generated by thermoelastic expansion in tissue sites acting as generation sources of initial ultrasonic waves. The ultrasonic waves thus formed reach the surface of the biological tissues with various delays and a photoacoustic image is obtained by imaging the same. In the following embodiments, the photoacoustic wave may refer to an acoustic wave generated by light absorption and the photoacoustic wave may include an ultrasonic wave.

Ultrasonic imaging is an established medical imaging method which diagnoses objects (e.g., diagnosing lesions of the human body) using ultrasonic waves. The ultrasonic image may be obtained by irradiating an object with an ultrasonic wave and receiving the ultrasonic wave returned from an inner material of the object. An ultrasonic image may include, for example, a B-mode image displaying a cross-sectional image of an object, an elasticity image showing elasticity information of the object, an M-mode image showing biological information of a specific part of the object, or a color doppler image to visualize the bloodstream in real-time, and the like.

The photoacoustic image may be used in conjunction with an ultrasonic image. Both anatomic structure and light absorbance may be determined through comparison and analysis between an ultrasonic image obtained by irradiating an ultrasonic wave to a specific site of an object and a photoacoustic image obtained by irradiating a laser to the specific site of the object.

FIG. 1 is a schematic view illustrating a problem occurring when a conventional photoacoustic probe irradiates light to an object.

The photoacoustic probe 10 receives a photoacoustic wave or photoacoustic signal generated in an object and thereby converts the same into an electric signal. In the description of the embodiments of the present invention, the photoacoustic wave may refer to a photoacoustic signal. The photoacoustic device includes the photoacoustic probe 10 to image the object using the electric signal converted by the photoacoustic probe 10.

Referring to FIG. 1, the photoacoustic probe 10 may be provided at the front surface thereof with an object contact unit 11 which contacts the object. The object contact unit 11 may be an acoustic lens which focuses an ultrasonic wave. The object contact unit 11 may have a first surface contacting the object, and a second surface, opposite of the second surface, which contacts the front surface of the photoacoustic probe 10.

A plurality of light scatterers 3 to scatter light are present in the object. When the object is irradiated with light having a specific wavelength, the radiated light 4 is transmitted into the object and some of the transmitted light 4 reaches a target material 1 to generate an acoustic wave, while the remaining light is scattered by the light scatterers 3 and is incident upon the object contact unit 11 (e.g., the first surface of the object contact unit 11). When the object contact unit 11 is made of a material absorbing the light 4, an acoustic wave is generated by light absorption in the object contact unit 11 and the generated acoustic wave is irradiated to the object again to form an artifact in a photoacoustic image.

The photoacoustic probe according to an embodiment of the present invention may be used for acquiring only a photoacoustic image, or both an ultrasonic wave image and a photoacoustic image. In the latter case, the photoacoustic probe has a configuration capable of both receiving and transmitting an ultrasonic wave. For this purpose, the photoacoustic probe may be realized as a conventional ultrasonic wave probe with a structure to transmit and receive an ultrasonic wave signal, and the photoacoustic probe may be combined with an optical fiber radiating light to enable irradiation of light and reception of ultrasonic waves to be realized by a single device.

Hereinafter, in the following embodiments, a photoacoustic probe for acquiring both an ultrasonic image and a photoacoustic image will be described. As an example for convenience of description, an acoustic wave generated by light absorption may include an ultrasonic wave and the object contact unit of the photoacoustic probe may include an acoustic lens. Also, in the following embodiments, "photoacoustic wave" and "ultrasonic wave" may be interchangeably used.

Figure 2A:
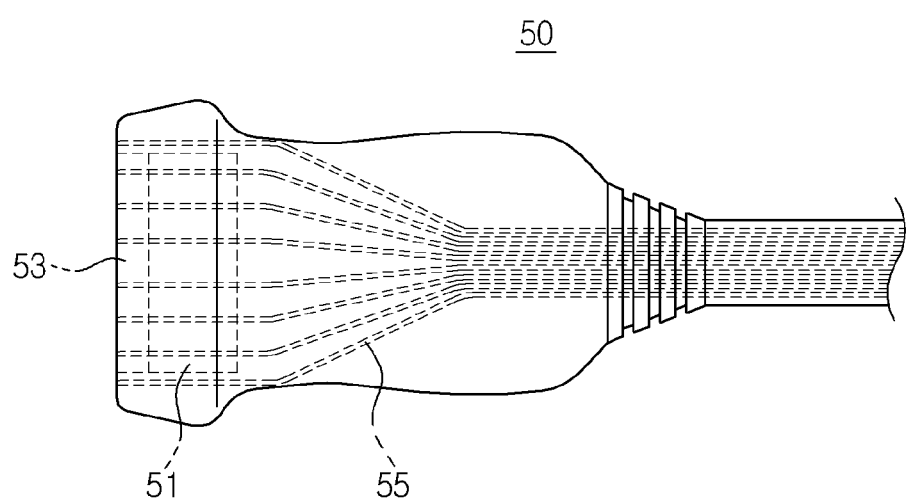
FIGS. 2A and 2B are a top view and a front view illustrating a structure of a photoacoustic probe capable of acquiring both a photoacoustic image and an ultrasonic wave image, respectively.
Figure 2B:
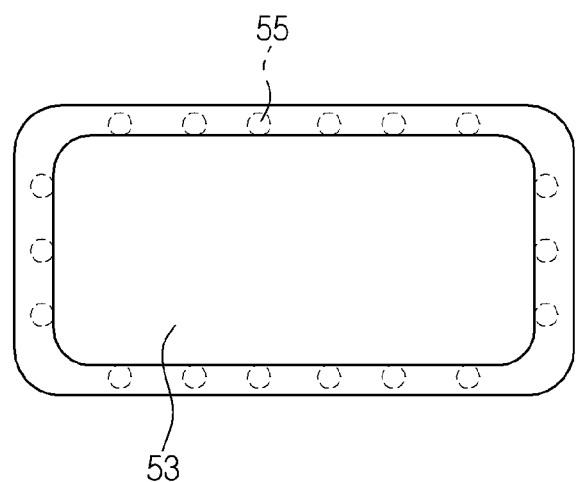

FIGS. 2A and 2B are a top view and a front view illustrating a structure of a photoacoustic probe suitable for, operable to, adapted to, configured to, capable of, etc. acquiring both a photoacoustic image and an ultrasonic wave image, respectively.

Referring to FIG. 2A, the probe 50 includes a piezoelectric module 51 to transmit and receive an ultrasonic wave, an acoustic lens 53 disposed at the front surface of the piezoelectric module 51 to focus the ultrasonic wave, and optical fibers 55 to irradiate light of a predetermined wavelength to an object. A light source to generate light may be provided in the photoacoustic device and a wavelength of light generated by the light source may be suitably selected while taking into consideration a target material present in the object.

The photoacoustic device may acquire an image of an object using a photoacoustic effect. As shown in FIGS. 2A and 2B, when the photoacoustic probe 50 transmits and receives an ultrasonic wave, the photoacoustic device produces an ultrasonic image of an object.

The piezoelectric module 51 may include a piezoelectric layer which performs interconversion between an electric signal and an acoustic signal, a matching layer disposed on the front surface of the piezoelectric layer and a backing layer disposed on the back surface of the piezoelectric layer.

A phenomenon in which a voltage is generated when mechanical pressure is applied to a predetermined object and a phenomenon in which mechanical deformation occurs when the voltage is applied are referred to as a piezoelectric effect and an inverse piezoelectric effect, respectively, and a material having these effects is referred to as a piezoelectric material. That is, the piezoelectric material converts electric energy into mechanical vibration energy and converts mechanical vibration energy into electric energy.

The piezoelectric layer may be made of a piezoelectric material, and may convert an electric signal into a mechanical vibration energy to generate an ultrasonic wave, upon receiving the electric signal, while converting an ultrasonic wave signal into an electric signal upon receiving the ultrasonic wave signal.

The piezoelectric material constituting the piezoelectric layer may include a ceramic of lead zirconate titanate (PZT), a PZMT single crystal containing a solid solution of lead magnesium niobate and lead titanate, a PZNT single crystal containing a solid solution of lead zinc niobate and lead titanate or the like.

The matching layer may be disposed on the front surface of the piezoelectric layer. The matching layer may reduce a difference in acoustic impedance between the piezoelectric layer and the object to thereby effectively transfer the ultrasonic wave generated by the piezoelectric layer to the object. The matching layer may include at least one layer and be divided into a plurality of units with a predetermined width together with the piezoelectric layer by a dicing process.

The backing layer may be disposed on the back surface of the piezoelectric layer. The backing layer may absorb an ultrasonic wave generated by the piezoelectric layer and block transmission of the ultrasonic wave toward the back surface of the piezoelectric layer to thereby prevent image distortion. The backing layer may include a plurality of layers in order to improve the reduction or blocking effect of ultrasonic waves.

The acoustic lens 53 may be disposed on the front surface of the piezoelectric module 51, and more specifically, the front surface of the matching layer to focus a transmitted or received ultrasonic wave.

The optical fibers 55 may irradiate light of a predetermined wavelength from a light source to the object. For example, as shown in FIG. 2B, a bundle of the optical fibers 55 may surround the piezoelectric module 51. This configuration is given as an example of the photoacoustic probe and the optical fibers 55 may be distributed at upper and lower sides and left and right sides of the piezoelectric module 51. Additionally, or alternatively, optical fibers may be disposed at other locations about the piezoelectric module.

A light source may be realized using a light-emitting device such as a semiconductor laser (LD), light emitting diode (LED), solid laser or gas laser to generate a specific wavelength component or monochromatic light including the component and may include a plurality of light sources to generate light with different wavelengths.

For example, in a case in which the photoacoustic probe measures a hemoglobin concentration of an object, light in a near-infrared wavelength region (about 650 nm to about 1,200 nm) is absorbed, although an optical absorbance property may be changed according to hemoglobin concentration. A laser to generate a single wavelength within the corresponding wavelength region may be used and an optical parametrical oscillator (OPO) laser to change a wavelength using a non-linear optical crystal may also be used.

Hereinafter, problems caused by light absorption of the acoustic lens and the embodiment of the present invention to solve the problems will be described in detail, based on the afore-mentioned photoacoustic probe having a structure, as an example.

Figure 3A:
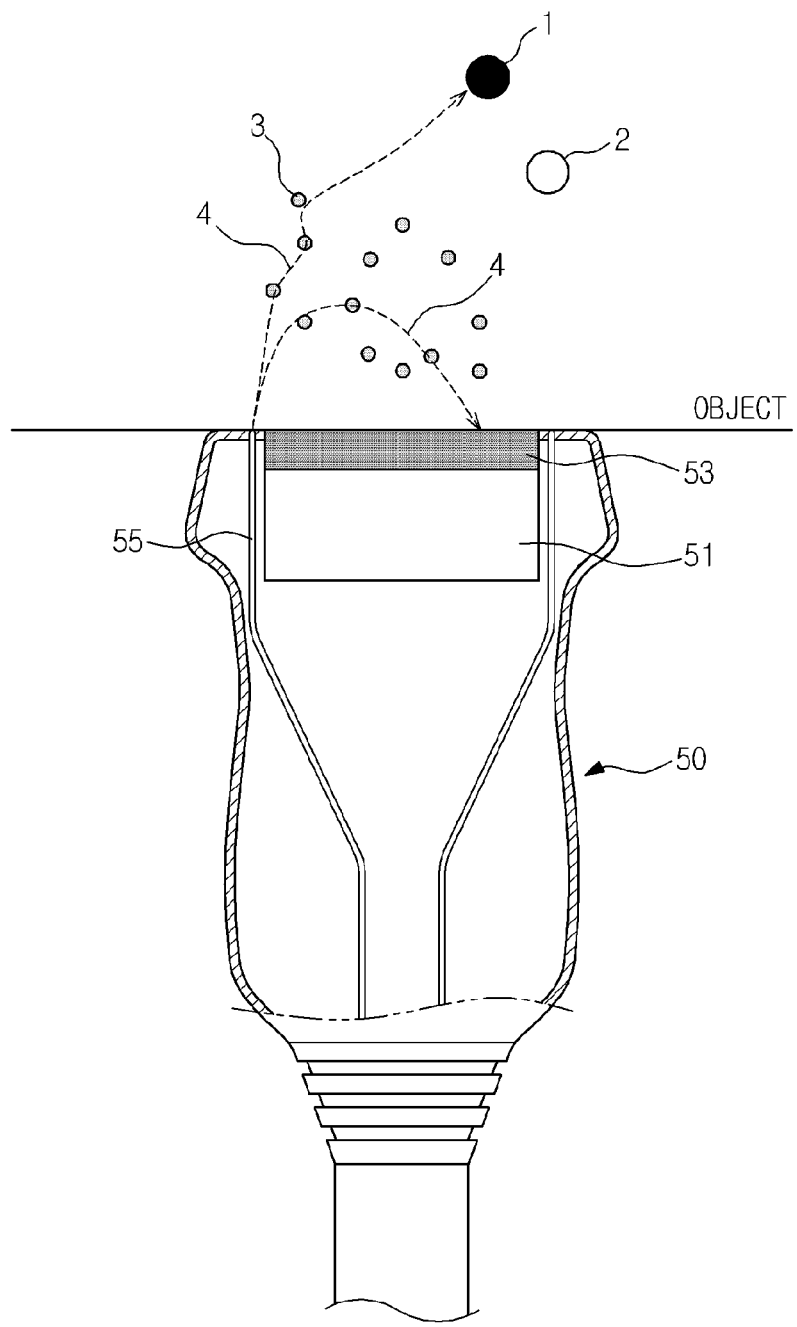
FIGS. 3A to 3C illustrate problems caused by irradiation of light from a photoacoustic probe to the object in detail.
Figure 3B:
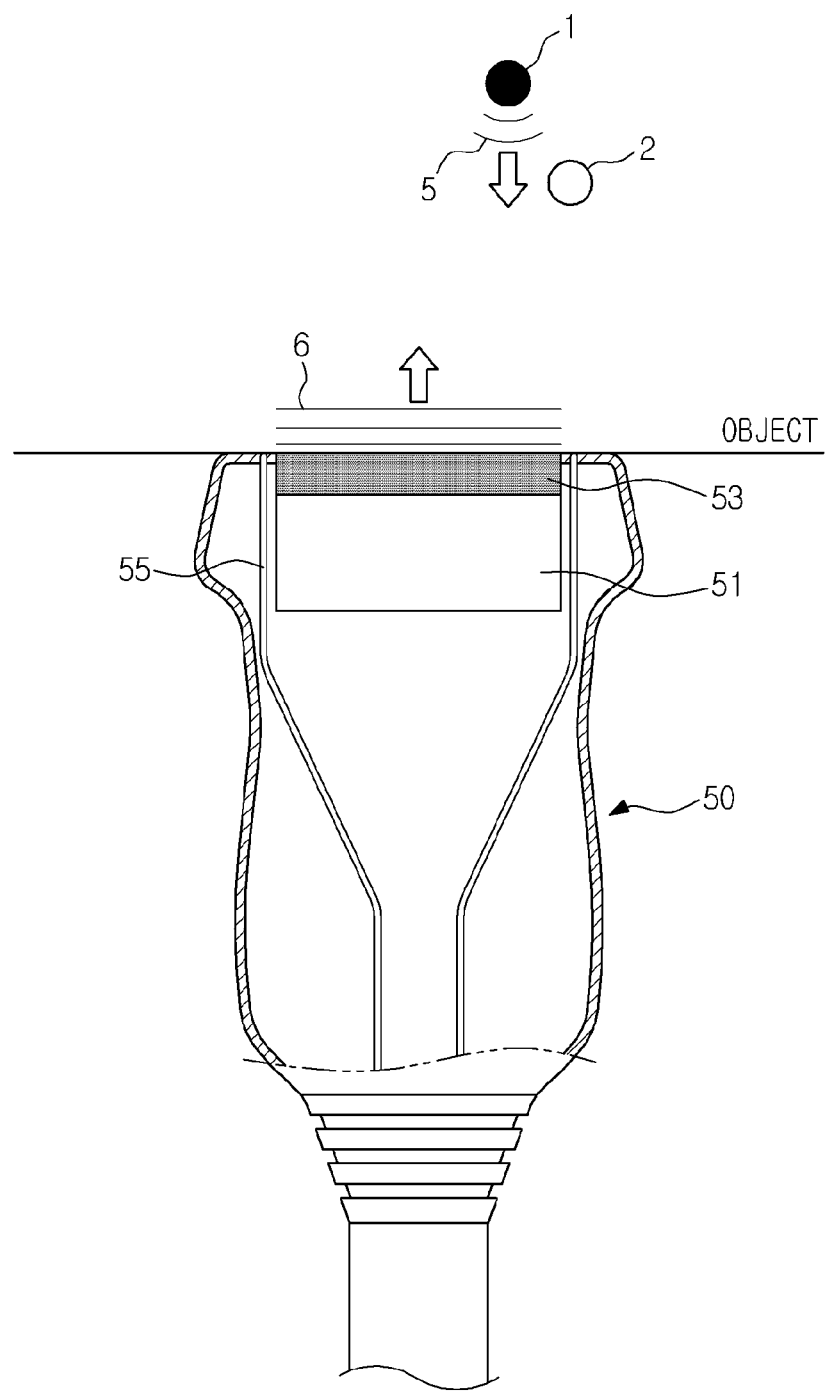
Figure 3C:
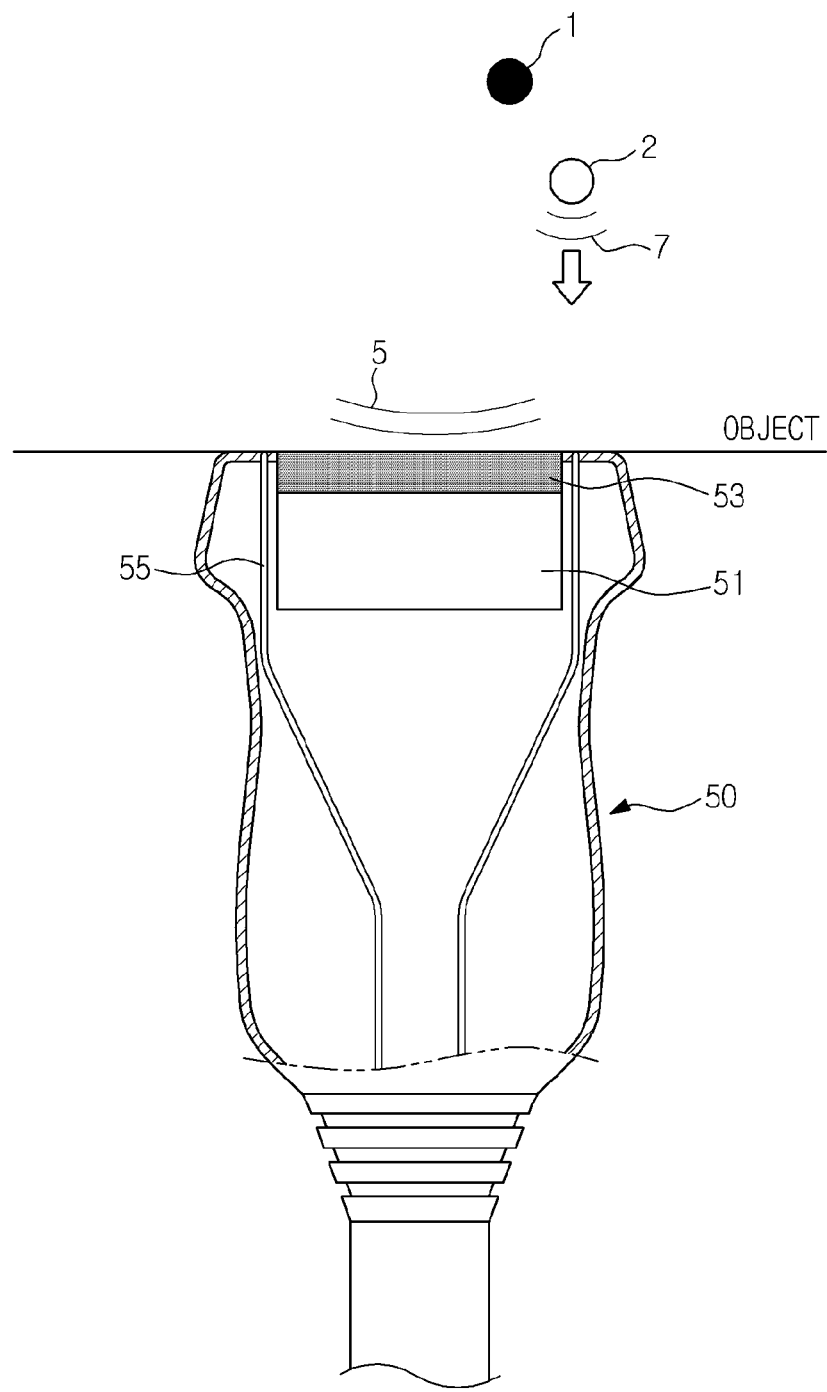

FIGS. 3A to 3C illustrate problems caused by irradiation of light from a photoacoustic probe to the object in detail. FIGS. 3A to 3C are sectional views illustrating a part of the photoacoustic probe.

Referring to FIG. 3A, the light 4 irradiated from optical fibers 55 is transmitted into an object, some thereof collide with light scatterers 3 and reach the target material 1 absorbing light, and the remaining light collides with the light scatterers 3 and is incident upon the acoustic lens 53.

Generally, the acoustic lens 53 has a certain color. When a pigment contained in the acoustic lens 53 absorbs light with a wavelength which falls within a wavelength of the light 4 irradiated from the optical fibers 55, or corresponds to the wavelength of the light 4, the incident light 4 is absorbed in the acoustic lens 53. As described above, when the target material 1 absorbs light, it generates an ultrasonic wave and the acoustic lens 53 also absorbs the incident light and thereby generates an ultrasonic wave 6, as shown in FIG. 3B.

That is, some of light 4 irradiated from the optical fibers 55 is absorbed in the target material 1 to generate an original photoacoustic wave 5, and the remaining light is absorbed in the acoustic lens 53, generating an unintended photoacoustic wave 6.

Referring to FIG. 3C, the original photoacoustic wave 5 generated by the target material 1 is incident upon the acoustic lens 53 and is converted into an electric signal in the piezoelectric module 51. The converted electric signal is used for formation of the photoacoustic image of the object. However, both an original photoacoustic wave 5 and an unintended photoacoustic wave 6 described in FIG. 3B are incident upon the acoustic lens 53. The unintended photoacoustic wave 6 described in FIG. 3B is transferred into the object, collides with the ultrasonic scatterer 2 present in the object and is returned as a reflection wave 7.

Accordingly, waves incident upon the photoacoustic probe 50 may include a photoacoustic wave generated by the target material 1 and a photoacoustic wave 7 reflected from a non-target material, (e.g., the ultrasonic scatterer 2). That is, the photoacoustic wave 7 generates an artifact in a finally produced photoacoustic image.

Figure 4:
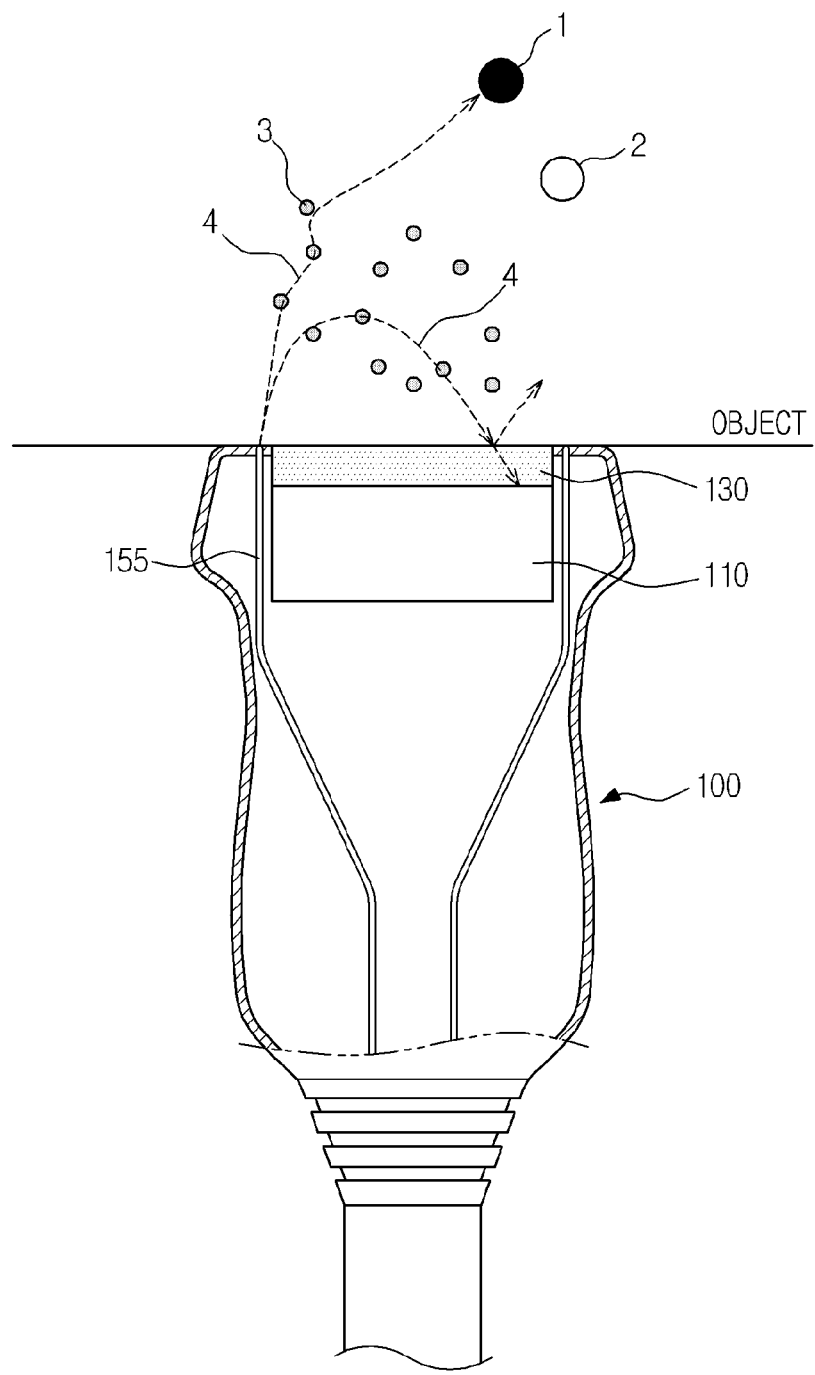
FIG. 4 is a sectional view illustrating an inner structure of a photoacoustic probe according to one embodiment of the present invention.

FIG. 4 is a sectional view illustrating an inner structure of a photoacoustic probe according to one embodiment of the present invention.

Referring to FIG. 4, the photoacoustic probe 100 according to an embodiment of the present invention includes a piezoelectric module 110 which performs interconversion between an electric signal and an acoustic signal, a flat acoustic lens 130 disposed on the front surface of the piezoelectric module 110 and an optical fiber 155 to radiate light to an object. As described above, the piezoelectric module 110 may include a matching layer, a piezoelectric layer and a backing layer. Meanwhile, the optical fiber 155 may be separately provided, instead of being included in the photoacoustic probe 100.

As described above, the artifact of the photoacoustic image by the non-target material 2 may be caused by light absorption of a pigment contained in the acoustic lens. Accordingly, the photoacoustic probe 100 according to an embodiment of the present invention includes an acoustic lens 130 which does not absorb light irradiated from the optical fiber 155. That is, the acoustic lens 130 shown in FIG. 4 may have colors different from those of the acoustic lens 53 shown in FIGS. 3A to 3C.

That is, in order to prevent the acoustic lens 130 from absorbing the light 4 irradiated from the optical fiber 155, a pigment contained in the acoustic lens 130 absorbs light with a wavelength different from that of light irradiated from the optical fiber 155, or a pigment is not contained in the acoustic lens 130. In the former case, a color of the acoustic lens 130 is changed into a different color, and in the latter case, the color is removed from the acoustic lens 130. For example, the acoustic lens 130 may be a first color and absorb light within a first wavelength, and the acoustic lens 130 does not correspond to (i.e., it is different from) a second wavelength of light which is emitted by the optical fiber 155.

For example, in a case in which the light 4 irradiated from the optical fiber 155 falls within a visible ray region having a wavelength shorter than green, the acoustic lens 130 contains a pigment absorbing light having a wavelength longer than a wavelength (about 532 nm) of green, and in a case in which the light 4 irradiated from the optical fiber 155 falls within red and infrared regions (for example, about 620 nm to about 1 mm), the acoustic lens 130 contains a pigment absorbing light having a wavelength shorter than about 600 nm. The optical fiber 155 may irradiate light having other wavelengths, and the disclosure is not limited to visible rays or infrared rays. The acoustic lens 130 may contain a pigment absorbing light of a wavelength different than a wavelength of light emitted by the optical fiber 155, or the acoustic lens 130 may not contain any pigment (e.g., the acoustic lens may be colorless).

As described above, when the acoustic lens 130 is designed or constructed to not absorb the light 4 irradiated from the optical fiber 155, generation of photoacoustic waves by light absorption of the acoustic lens 130 may be prevented and artifacts in the photoacoustic image are thus reduced.

Figure 5:
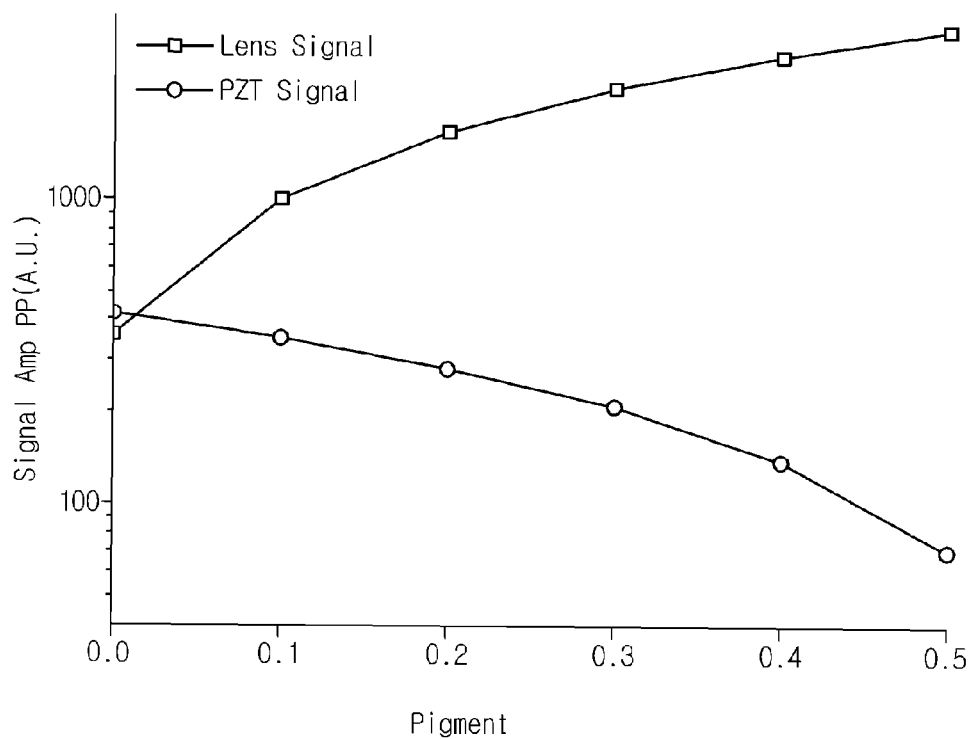
FIG. 5 is a graph showing intensities of a lens signal and a PZT signal as a function of a pigment ratio of an acoustic lens.

FIG. 5 is a graph showing intensities of a lens signal and a PZT signal as a function of a pigment ratio of an acoustic lens. For example, the pigment ratio may increase as the acoustic lens absorbs more light. Here, the pigment of the acoustic lens may be a pigment which absorbs the light 4 irradiated from the optical fiber 155.

Referring to FIG. 4 again, when the acoustic lens 130 does not absorb the light 4 irradiated from the optical fiber 155, a part of the light 4 incident upon the acoustic lens 130 passes through the acoustic lens 130 and reaches the piezoelectric module 110. In this case, the piezoelectric module 110 also absorbs the light 4 and generates a photoacoustic wave In the graph of FIG. 5, the photoacoustic wave signal which is incident again by light absorption of the acoustic lens 130 is referred to as a lens signal and a photoacoustic wave signal which is incident again by light absorption of the piezoelectric module 110 is referred to as a PZT signal. That is, a photoacoustic wave which is generated by the light absorption of the acoustic lens 130, is then reflected from the ultrasonic wave scatterers and is returned back, is referred to as the lens signal. A photoacoustic wave which is generated by light absorption of the piezoelectric module 110, is reflected from the ultrasonic wave scatter and is returned back, is referred to as the PZT signal.

Referring to FIG. 5, as the pigment ratio of the acoustic lens 130 decreases (i.e., the amount of light absorbed by the acoustic lens decreases), the intensity of the lens signal decreases, but the intensity of the PZT signal increases (i.e., the amount of light absorbed by the piezoelectric module increases). However, as shown in the graph of FIG. 5, a decrease in intensity of the lens signal with a decrease of the pigment ratio is greater than an increase in intensity of the PZT signal with a decrease of the pigment ratio. That is, the amount of light absorbed overall by the acoustic lens and piezoelectric module may decrease.

Accordingly, in order to reduce artifacts in the photoacoustic image, as in the embodiment of the present invention, the acoustic lens 130 does not contain a pigment or contains a pigment which does not absorb the light 4 irradiated from the optical fiber 155.

Figure 6:
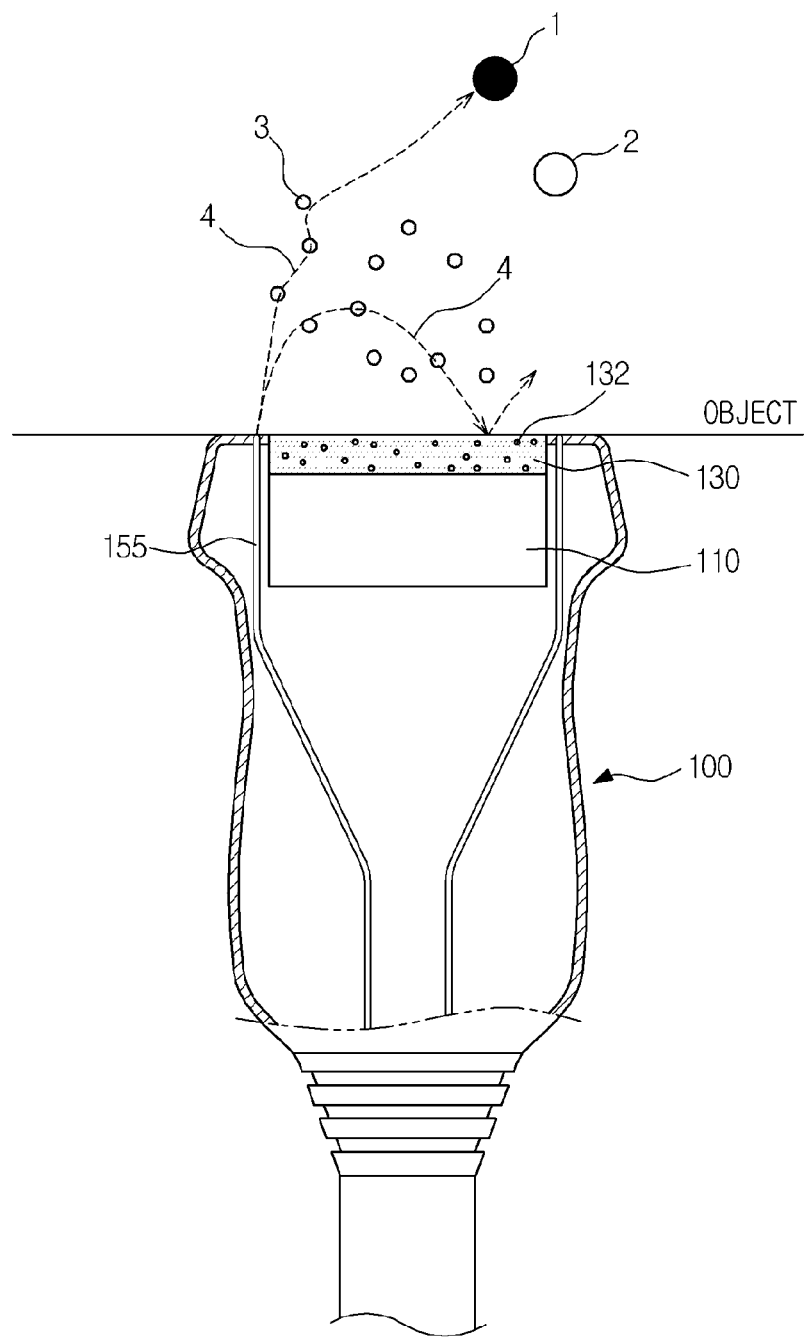
FIG. 6 is a sectional view illustrating a photoacoustic probe including a light scattering particle according to one embodiment of the present invention.

FIG. 6 is a sectional view illustrating a photoacoustic probe including a light scattering particle according to an embodiment of the present invention.

Referring to FIG. 6, the acoustic lens 130 may include a light scattering particle 132 in order to reduce a light absorption effect of the piezoelectric module 110. The light scattering particle 132 may have a submicron size and may include titanium dioxide ($TiO_2$), aluminum dioxide ($AlO_2$), silicon dioxide ($SiO_2$), and the like. The type of the light scattering particle 132 is not limited to these materials and various other types of light scattering particles 132 may be included in the acoustic lens 130.

Meanwhile, in order to maintain acoustic properties of the acoustic lens 130 before and after insertion of the light scattering particle 132, a volume ratio of the light scattering particle 132 may be adjusted to about 6 percent or less, based on the acoustic lens 130.

When the light scattering particle 132 is included in the acoustic lens 130, the light 4 incident upon the acoustic lens 130 may be scattered by the light scattering particle 132 and an amount of light reaching the piezoelectric module 110 is thus reduced. The photoacoustic probe 100 according to the embodiment described in FIG. 6 reduces both light absorption effect of the acoustic lens 130 and light absorption effect of the piezoelectric module 110 to thereby minimize artifacts of the photoacoustic image on the object.

The photoacoustic device according to an embodiment of the present invention includes the photoacoustic probe 100 according to the afore-mentioned embodiment, which reduces artifacts by light absorption effect of the acoustic lens 130 and improves image quality, upon receiving a signal from the photoacoustic probe 100 and generating a photoacoustic image.

Figure 7A:
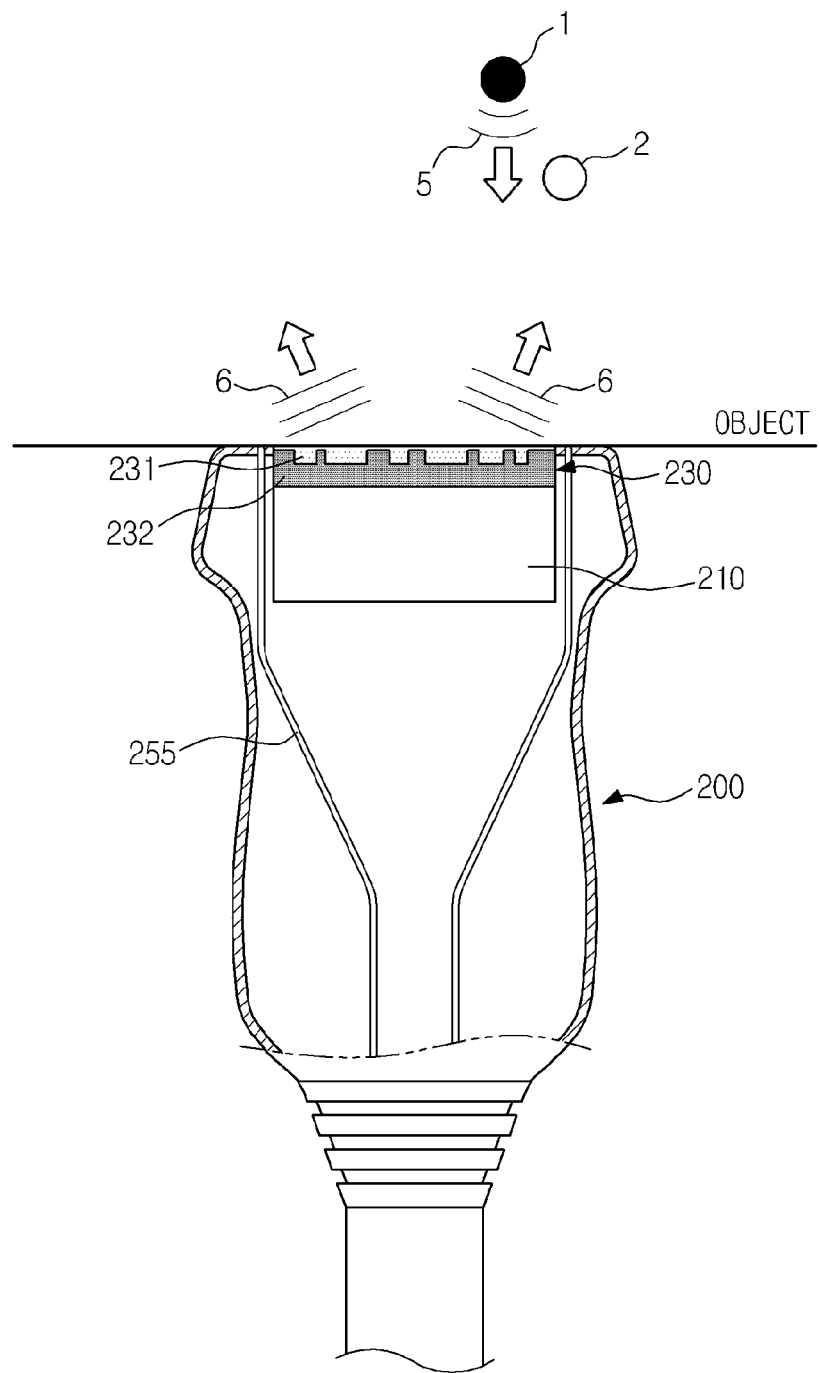
FIGS. 7A and 7B are sectional views illustrating an inner structure of the photoacoustic probe according to another embodiment of the present invention.
Figure 7B:
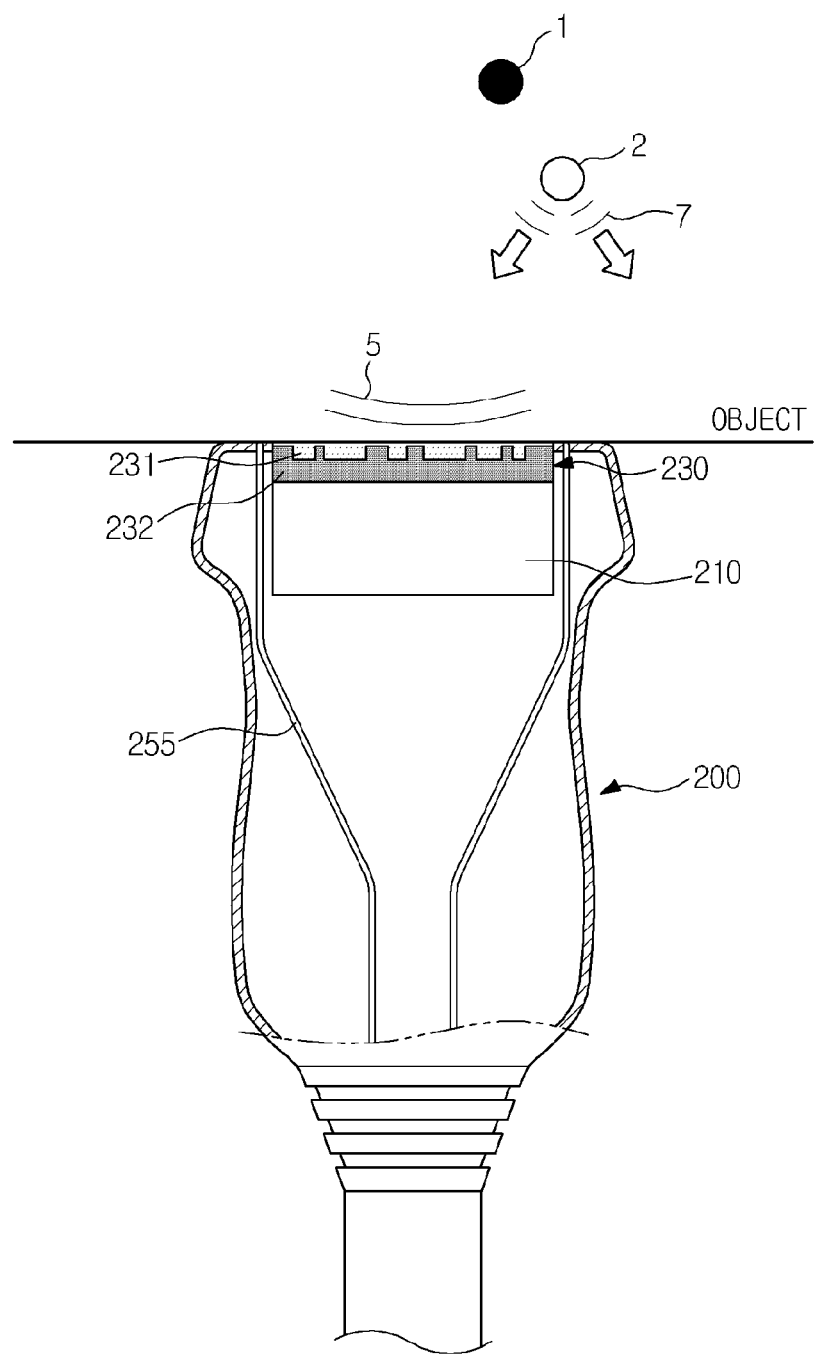

FIGS. 7A and 7B are sectional views illustrating an inner structure of the photoacoustic probe according to an embodiment of the present invention.

Referring to FIGS. 7A and 7B, the photoacoustic probe 200 according to an embodiment of the present invention includes a piezoelectric module 210 which performs inter-conversion between an electric signal and an acoustic signal, an acoustic lens 230 disposed on the front surface of the piezoelectric module 210 and an optical fiber 255 to irradiate light to an object. The piezoelectric module 210 may include a matching layer, a piezoelectric layer and a backing layer. Meanwhile, the optical fiber 255 may be separately provided, instead of being included in the photoacoustic probe 100.

The acoustic lens 230 may include a non-absorption portion 231 not absorbing the light 4 irradiated from the optical fiber 255 and an absorption portion 232 absorbing the light 4 irradiated from the optical fiber 255. The non-absorption portion 231 may be disposed at a side contacting the object, while the absorption portion 232 may be disposed at the rear surface of the non-absorption portion 231. The acoustic lens 230 may have a flat shape.

The non-absorption portion 231 and the absorption portion 232 may have the same acoustical properties, but have different optical properties. For this purpose, the non-absorption portion 231 and the absorption portion 232 may be made of the same material, but have different colors.

Specifically, as shown in FIG. 4, the non-absorption portion 231 may contain a pigment not absorbing the light irradiated from the optical fiber 255 or does not contain a pigment. That is, the non-absorption portion 231 may have a color with a different wavelength from the light 4 irradiated from the optical fiber 255, or may not have a color.

The absorption portion 232 may contain a pigment having an intended color of the acoustic lens 230. There is a case in which the acoustic lens 230 renders a specific color, for example, a color is used in order to render a corporate identity (CI) of a product. In this case, the absorption portion 232 may contain a pigment having a specific color, thereby enabling the acoustic lens 230 to render a specific color in an exterior part.

A contact surface between the non-absorption portion 231 and the absorption portion 232 may have a step (e.g., similar to a shape of a step function). That is, the contact surface between the non-absorption portion 231 and the absorption portion 232 may not have a flat surface but instead may have a protrusion/groove or an irregular shape. The step may be periodically repeated and the period may be irregular. For example, the contact surface between the non-absorption portion 231 and the absorption portion 232 may have a saw-tooth shape, a sinusoidal shape, a lens (concave/convex) shape, and the like. A width of each step, tooth, etc., may be uniform or may vary. A height of each step, tooth, etc., may be uniform or may vary. A period of each step, tooth, etc., may be uniform or may vary. A detailed explanation thereof will be given with reference to FIG. 8 later.

When a part of light irradiated from the optical fiber 255 is absorbed in the target material 1 and the other part thereof is incident upon the acoustic lens 230 through the light scatterer, as shown in FIG. 7A, an original photoacoustic wave 5 may be generated in the target material 1 and an unintended photoacoustic wave 6 may be generated in the acoustic lens 230. The generated photoacoustic wave 6 may be diffracted by the step structure of the acoustic lens 230 and may be transferred into the object in the form of a diffraction wave not parallel to the surface of the acoustic lens 230.

A reflection wave 7 of the photoacoustic wave 6 transferred in the form of a diffraction wave may be reflected in a plurality of directions and the photoacoustic wave 6 thus becomes weak, although the photoacoustic wave 6 collides with the non-target material 2 scattering an ultrasonic wave, as shown in FIG. 7B. Accordingly, generation of artifacts in the photoacoustic image of the object is reduced. That is, as shown in FIG. 7B, a reflection wave reflected from a non-target material may not be directed toward or reach the acoustic lens 230, or may be weakened to an extent such that the reflection wave has a lesser effect. Hereinafter, a configuration of the acoustic lens 230 will be described with reference to FIG. 8 in detail.

Figure 8:
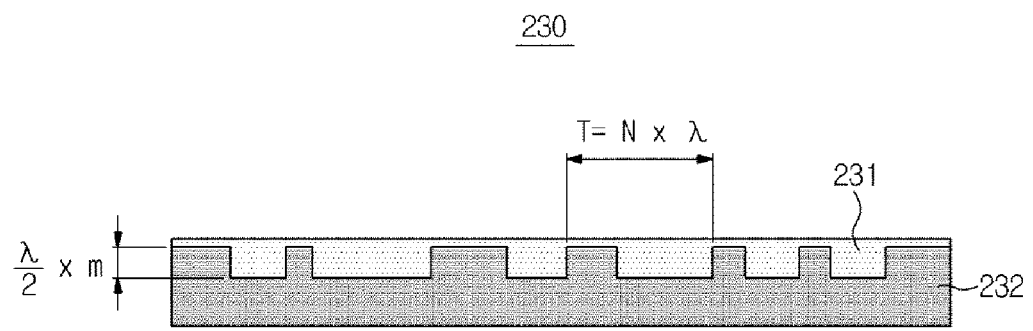
FIG. 8 is an enlarged view illustrating a configuration of an acoustic lens having a step.

FIG. 8 is an enlarged view illustrating a configuration of an acoustic lens having a step.

Referring to FIG. 8, a height of the step of the acoustic lens 230 may be m-fold of half of a wavelength (λ) of a photoacoustic wave generated by absorption of light incident upon the acoustic lens 230 by the absorption portion 232 and m may be an odd number. The step may be repeated in an irregular period and the period (T) of the step may be an integer number (N)-fold of the wavelength (λ) of photoacoustic wave and the integer number (N) may be random. A relation between the height of the step and the period (T) and the wavelength (λ) of the photoacoustic wave may be based on a diffraction phenomenon of the wave field.

When light irradiated from the optical fiber 255 is incident upon the acoustic lens 230, the photoacoustic wave generated by light absorption of the absorption portion 232 may be formed along the surface of the absorption portion 232, and an intensity of the photoacoustic wave of this case is the same as a case having no step structure, is distributed to randomly have a phase difference of about 0 to about 180 degrees and may be transferred to the object in the form of a diffraction wave not parallel to the surface of the acoustic lens 230.

FIGS. 9A to 9D illustrate a process for manufacturing an acoustic lens according to another embodiment of the present invention.

Figure 9A:
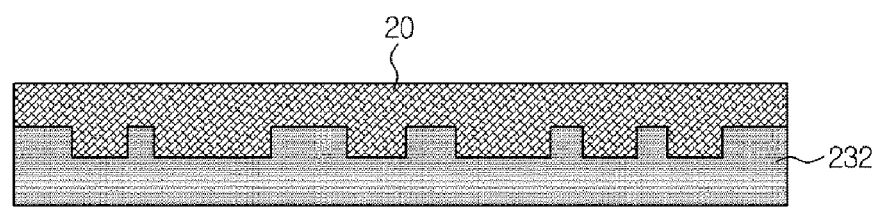
FIGS. 9A to 9D illustrate a process for manufacturing an acoustic lens according to another embodiment of the present invention.

Referring to FIG. 9A, a material for forming the absorption portion 232 may be inserted into a mold 20 corresponding to the shape of the absorption portion 232. The material for forming the absorption portion 232 may be, for example, a silicone rubber containing a pigment. The shape corresponding to the shape of the absorption portion 232 may be reverse to the shape of the absorption portion 232. For example, a groove of the absorption portion 232 corresponds to a protrusion of the mold 20 and a protrusion of the absorption portion 232 corresponds to a groove of the mold 20. For example, a peak or step of the absorption portion 232 may correspond to a trough of the mold 20.

Figure 9B:
Figure 9C:
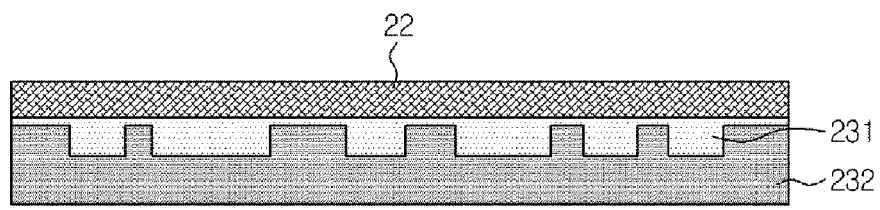

When the absorption portion 232 is completely cured, the mold 20 is removed, as shown in FIG. 9B. Also, as shown in FIG. 9C, a material for forming the non-absorption portion 231 may be inserted into the absorption portion 232. That is, the material for forming the non-absorption portion 231 fills the groove of the absorption portion 232 and a flat mold 22 is placed thereon. As a result, the material not absorbing light constitutes the surface of the acoustic lens 130. As an example of the material constituting the non-absorption portion 231, a silicone rubber containing no pigment may be used.

Figure 9D:
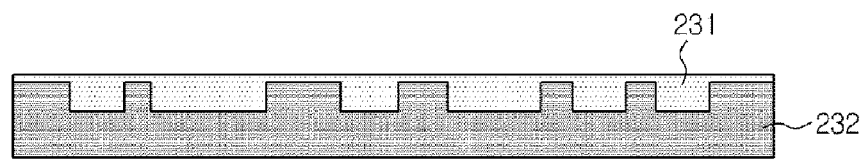

When the non-absorption portion 231 is completely cured, the mold 22 is removed, as shown in FIG. 9D. As shown in FIGS. 9A to 9D, the acoustic lens 230 may be prepared by double injection (e.g., by using one mold for an absorption portion and another mold for a non-absorption portion), but this method is given as an example of the method for manufacturing the acoustic lens 230, but the embodiment of the present invention is not limited thereto.

Figure 10:
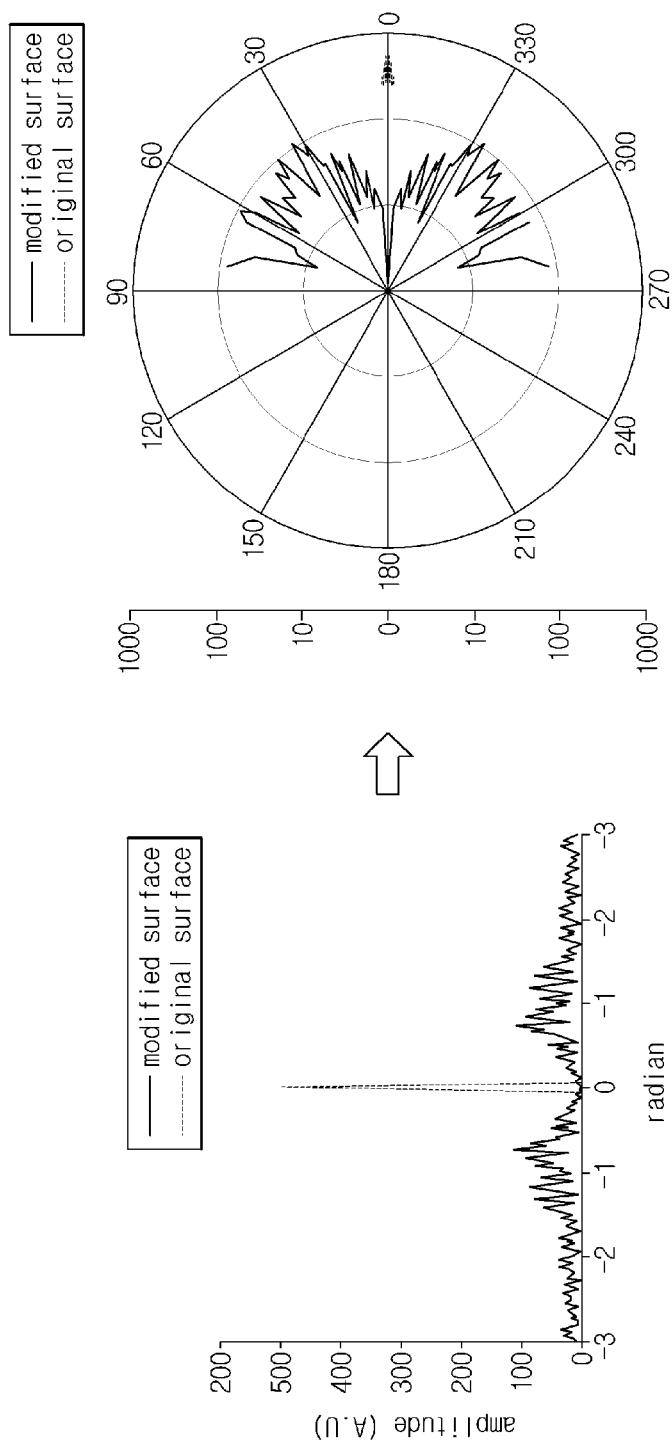
FIG. 10 illustrates a change in radiation direction of photoacoustic waves depending on configuration of the acoustic lens according to another embodiment of the present invention.

FIG. 10 illustrates a change in radiation direction of photoacoustic waves depending on a construction or configuration of the acoustic lens according to an embodiment of the present invention. A polar chart is shown in the right side of FIG. 10.

As can be seen from FIG. 10, the photoacoustic wave irradiated from a general acoustic lens 53 may be irradiated in a specific direction or at a specific angle, but the photoacoustic wave irradiated from the acoustic lens 230 having a step structure spreads at a great angle and the effect thereof is reduced.

Meanwhile, the photoacoustic device according to an embodiment of the present invention includes the photoacoustic probe 200 according to the afore-mentioned example embodiments, and reduces artifacts by light absorption effect of the acoustic lens 130 and improves an image quality, upon receiving a signal from the photoacoustic probe 200 and generating a photoacoustic image.

In the example embodiments described above, the object contact unit may refer to an acoustic lens, but the embodiments of the present invention are not limited thereto. That is, when an additional layer is provided on the front surface of the acoustic lens, the layer may serve as an object contact unit, and the structure of FIG. 4 and structures of FIGS. 7A to 7C may be applied. More specifically, the object contact unit may contain a pigment not absorbing light irradiated from the optical fiber or does not contain a pigment. In another embodiment, the object contact unit includes an absorption portion absorbing light irradiated from the optical fiber and a non-absorption portion not absorbing light irradiated from the optical fiber, and the contact surface of the absorption portion and the non-absorption portion may have a step shape.

As is apparent from the above description, a photoacoustic probe and a photoacoustic device including the same according to example embodiments of the present invention reduce artifacts in photoacoustic images caused by photoacoustic waves generated in the photoacoustic probe. The photoacoustic probe and photoacoustic device including the same according to example embodiments may achieve reduced artifacts and improved image quality without mounting a separate device, and instead by changing a configuration or structure of the object contact unit provided in the photoacoustic probe. The light source which emits light toward the object may emit light of various wavelengths. The photoacoustic probe may include an object contact unit (e.g., an acoustic lens) which absorbs light of a different wavelength than that of the wavelength of a light emitted by the light source and/or the wavelength of a light absorbed by the object. In an additional or alternative embodiment, the photoacoustic probe may be suitable for, operable to, adapted to, configured to, capable of, etc., changing out or modifying or replacing the object contact unit (e.g., the acoustic lens) according to the wavelength of the light emitted by the light source and/or according to the wavelength of the light absorbed by the object, in the event that the wavelength of the light emitted by the light source changes and/or in the event that the wavelength of the light absorbed by the object changes.

The disclosure herein has described one or more embodiments in which a photoacoustic probe and a photoacoustic device may be used in medical applications to obtain an image of and/or diagnose biological tissues of a subject, for the treating and diagnosing of the subject (e.g., humans, animals, and other lifeforms). However, the photoacoustic probe and photoacoustic device disclosed herein need not be limited to the medical field, and may be used in other fields, and may be used on any object including for industrial applications to examine internal characteristics and structures of an object.

The photoacoustic probe and photoacoustic device according to the above-described example embodiments may use one or more processors. For example, a processing device may be implemented using one or more general-purpose or special purpose computers, such as, for example, a processor, a controller and an arithmetic logic unit, a central processing unit (CPU), a graphics processing unit (GPU), a digital signal processor (DSP), a microcomputer, a field programmable array, a programmable logic unit, an application-specific integrated circuit (ASIC), a microprocessor or any other device capable of responding to and executing instructions in a defined manner.

Although a example embodiments disclosed herein have been shown and described, it would be appreciated by those skilled in the art that changes may be made to these embodiments without departing from the principles and spirit of the invention, the scope of which is defined in the claims and their equivalents.

What is claimed is:

1. A photoacoustic probe, comprising:
    a piezoelectric module configured to convert a photoacoustic signal received from an object, which absorbs light of a predetermined wavelength and which is disposed inside a subject, into an electric signal; and
    an object contact unit disposed on a front surface of the piezoelectric module, the object contact unit comprising an acoustic lens to focus the photoacoustic signal and configured to come into contact with the subject and to not absorb the light of the predetermined wavelength.

2. The photoacoustic probe according to claim 1, wherein the photoacoustic signal is input through the object contact unit into the piezoelectric module.

3. The photoacoustic probe according to claim 2, wherein the object contact unit comprises a pigment not absorbing the light of the predetermined wavelength.

4. The photoacoustic probe according to claim 3, wherein the pigment has a color having a wavelength different from the predetermined wavelength.

5. The photoacoustic probe according to claim 1, wherein the object contact unit does not comprise a pigment.

6. The photoacoustic probe according to claim 1, wherein the object contact unit comprises a light scattering particle.

7. The photoacoustic probe according to claim 6, wherein the light scattering particle includes at least one light scattering particle selected from the group consisting of titanium dioxide (TiO2), aluminum dioxide (AlO2) and silicon dioxide (SiO2).

8. The photoacoustic probe according to claim 6, wherein the light scattering particle has a submicron size.

9. The photoacoustic probe according to claim 6, wherein the light scattering particle has a volume ratio of about 6% or less with respect to the object contact unit.

10. The photoacoustic probe according to claim 1, wherein the object contact unit has a flat shape.

11. The photoacoustic probe according to claim 1, wherein the piezoelectric module includes:
 a piezoelectric layer which performs interconversion between an electric signal and an acoustic signal,
 a matching layer disposed on a front surface of the piezoelectric layer, and
 a backing layer disposed on a back surface of the piezoelectric layer, and
 the acoustic lens is disposed on the front surface of the piezoelectric module.

12. The photoacoustic probe according to claim 1, wherein the object contact unit comprises an absorption portion and a non-absorption portion, the absorption portion having a higher absorbance to light of the predetermined wavelength than the non-absorption portion, and a contact surface of the absorption portion and the non-absorption portion has a step and the absorption portion is provided between the non-absorption portion and the piezoelectric module.

13. The photoacoustic probe according to claim 12, wherein the absorption portion comprises a pigment which absorbs the light of the predetermined wavelength, and the non-absorption portion comprises a pigment which does not absorb the light of the predetermined wavelength.

14. The photoacoustic probe according to claim 12, wherein a height of the step is an odd fold of half of a wavelength of a photoacoustic wave generated by the absorption portion.

15. The photoacoustic probe according to claim 12, wherein the step formed on the contact surface between the absorption portion and the non-absorption portion is repeated in an irregular period.

16. The photoacoustic probe according to claim 15, wherein the period of the step is a multiple of the wavelength of the photoacoustic wave generated by the absorption portion.

17. A photoacoustic device, comprising:
 a probe configured to receive a photoacoustic signal from an object disposed inside a subject and which absorbs light of a first wavelength, the probe including:
  a piezoelectric module configured to convert the photoacoustic signal into an electric signal, and
  an object contact unit disposed on one side of the piezoelectric module, wherein the object contact unit comprises an acoustic lens to focus the photoacoustic signal and is configured to come into contact with the subject and to absorb light of a second wavelength.

18. The photoacoustic device of claim 17 further comprising:
 a light source to emit light of the first wavelength toward the object.

19. The photoacoustic device of claim 17, wherein the object contact unit includes a first color to absorb light of the second wavelength.

20. The photoacoustic device of claim 17, wherein the object contact unit includes a light scattering particle having a volume ratio of about 6% or less with respect to the object contact unit.

21. The photoacoustic device of claim 17, wherein the object contact unit includes an absorption portion and a non-absorption portion, the absorption portion having a higher absorbance to light of the first wavelength than the non-absorption portion.

22. The photoacoustic device of claim 21, wherein the absorption portion is disposed between the piezoelectric module and the non-absorption portion, and
 the non-absorption portion includes a different color than the absorption portion.

23. The photoacoustic device of claim 21, wherein the absorption portion is formed with at least one protrusion shaped to fit into at least one groove of the non-absorption portion.

24. The photoacoustic device of claim 21, wherein the absorption portion includes a second color to absorb light of the first wavelength, and the non-absorption portion includes the first color.

* * * * *